United States Patent [19]
Clark et al.

[11] Patent Number: 5,304,660
[45] Date of Patent: Apr. 19, 1994

[54] PYRAN DERIVATIVES

[75] Inventors: Stanley F. Clark; Ronald H. Jones; Christopher G. Newton, all of Dagenham, United Kingdom

[73] Assignee: Rhone-Poulenc Rorer S.A., Antony Cedex, France

[21] Appl. No.: 867,708

[22] PCT Filed: Jan. 7, 1991

[86] PCT No.: PCT/EP91/00012
§ 371 Date: Aug. 11, 1992
§ 102(e) Date: Aug. 11, 1992

[87] PCT Pub. No.: WO91/10672
PCT Pub. Date: Jul. 25, 1991

[30] Foreign Application Priority Data
Jan. 8, 1990 [GB] United Kingdom ............... 9000372
Jan. 16, 1990 [GB] United Kingdom ............... 9000890

[51] Int. Cl.$^5$ .......................................... C07D 309/10
[52] U.S. Cl. ..................................................... 549/417
[58] Field of Search ....................................... 549/417

[56] References Cited
U.S. PATENT DOCUMENTS
4,677,211  6/1987  Jewell, Jr. et al. .

FOREIGN PATENT DOCUMENTS
0326386  8/1989  European Pat. Off. .

OTHER PUBLICATIONS
Canadian Journal of Chemistry, vol. 42, pp. 532–538, 1964, The Bromination and Halogenomethoxylation of D α Glucal Triacetate.
J. Org. Chem., vol. 49, No. 21, pp. 3994–4003, 1984, Synthetic and Biological Studies of Compactin and Related Compounds. 2. Synthesis of the Lactone.

*Primary Examiner*—Nicky Chan
*Attorney, Agent, or Firm*—Raymond S. Parker, III; Martin F. Savitzky

[57] ABSTRACT

The invention provides compounds of formula (I) wherein $R^1$ represents alkyl, $R^2$ represents an acid-labile protecting group and $X^1$ represents a halogen atom, which are useful in the synthesis of mevalonic acid derivatives.

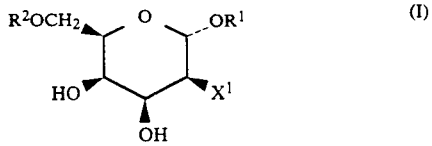

8 Claims, No Drawings

PYRAN DERIVATIVES

DESCRIPTION

This invention relates to new intermediates, to a process for their preparation, to their use in the preparation of pharmaceuticals, and to pharmaceuticals prepared therefrom.

The new intermediates of the present invention are the compounds of general formula I hereinafter depicted wherein $R^1$ represents a straight- or branched-chain alkyl group containing from 1 to about 4 carbon atoms, preferably methyl or isopropyl, $R^2$ represents an acid-labile protecting group, preferably a triphenylmethyl group, and $X^1$ represents a halogen, preferably bromine or iodine, atom.

The compounds of formula I are key intermediates in a new reaction sequence which permits the stereospecific preparation of analogues of mevalonic acid without the necessity to use potentially hazardous mercury compounds employed in previously known processes described, for example, by Rosen et al, J. Org. Chem., 1984, 49, 3994–4003 and Corey et al, J. Am. Chem. Soc., 1980, 102, 1439.

The said analogues of mevalonic acid are valuable pharmaceutically active compounds, more especially competitive inhibitors of 3-hydroxy-3-methylglutaryl coenzyme A reductase, and are consequently inhibitors of cholesterol biosynthesis and as a result are of use in the prevention or treatment of hypercholesterolaemic and hyperlipoproteinaemic states, atherosclerosis and associated conditions.

Examples of such mevalonic acid analogues are described, for example, in the specifications of our granted South African Patents Nos. 88/5852 and 89/0645 and of their equivalents in other countries, for example United States Patent Applications Nos. 07/230,038, now U.S. Pat. No. 4,933,350, and 07/302,389, now abandoned in favor of a file wrapper continuation Ser. No. 494,956, now U.S. Pat. No. 5,004,747.

According to a feature of the present invention, compounds of formula I are prepared by the reaction of compounds of general formula II hereinafter depicted, wherein $R^2$ is as hereinbefore defined, with a halogenating agent, e.g. N-iodosuccinimide when $X^1$ represents iodine and N-bromosuccinimide when $X^1$ represents bromine, and the appropriate alcohol of the general formula:

$$R^1OH \qquad \qquad III$$

wherein $R^1$ is as hereinbefore defined. The alcohol of formula III may act as the solvent medium alone or with one or more additional solvents such as polar aprotic solvents, e.g. acetonitrile.

According to a further feature of the present invention, the compounds of formula I are then hydrogenated, using a hydrogenation catalyst such as palladium on charcoal or Raney nickel, in the presence of a base, for example triethylamine or an alkali metal hydroxide, e.g. potassium hydroxide, to form compounds of general formula IV hereinafter depicted, wherein $R^1$ and $R^2$ are as hereinbefore defined The hydrogenation is preferably carried out in an organic solvent, for example a lower alkanol containing up to about 3 carbon atoms, e.g. methanol or ethanol, especially when an alkali metal hydroxide is used as the base, a lower ester, e.g. methyl or ethyl acetate, or an aromatic solvent, e.g. toluene, at about 10°–60° C., preferably 20°–50° C. and preferably at about 40–60 p.s.i.

According to a further feature of the present invention, compounds of formula IV are elaborated to prepare the said mevalonic acid analogues, by the application or adaptation of known methods Compounds of formula II may be prepared by the application or adaptation of known methods, for example as described by Fraser-Reid et al, Can. J. Chem., 51, 3950 (1973).

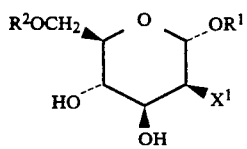

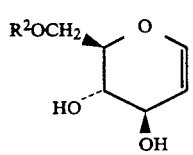

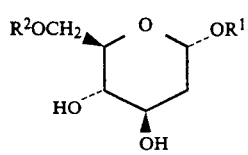

The following Examples illustrate the present invention.

Nuclear Magnetic Resonance (NMR) spectra are conducted in solution in $CDCl_3$ and the chemical shifts are given in ppm with tetramethylsilane as reference. The following abbreviations are used: "s" means "singlet", "d" means "doublet", "q" means "quadruplet" and "m" means "multiplet".

EXAMPLE 1

A stirred solution of 3α,4β-dihydroxy-2β-triphenylmethoxymethyl-3,4-dihydropyran (5 g) in methanol (50 ml) at 0° C. was treated with N-iodosuccinimide (4.4 g) during 15 minutes, maintaining the temperature at 0° to 5° C., and the resulting solution was stirred for a further period of 90 minutes, still maintaining the temperature at 0° to 5° C. It was then allowed to warm up overnight. The mixture was evaporated to dryness under vacuum at 40° C. The residue was treated with dichloromethane (50 ml) and water (30 ml) and then treated slowly with solid sodium thiosulphate (ca. 1 g) until the mixture was decolourised. The organic layer was separated off, washed with water (30 ml), dried over magnesium sulphate, and evaporated to dryness, to give 3α,4β-dihydroxy-5β-iodo-6α-methoxy-2β-triphenyl methoxymethyltetrahydropyran (6.19 g), m.p. 78°–82° C. [NMR: s,1.57; d,2.39; d,2.42; s,2.76; s,3.36; m,3.37–3.50; d,4.46; s,5.09; m,7.20–7.35; m,7.45–7.50].

EXAMPLE 2

By proceeding in a manner similar to that hereinbefore described in Example 1, but replacing the methanol by a mixture of acetonitrile (50 ml) and methanol (1 g), there was obtained 3α,4β-dihydroxy-5β-iodo-6α-methoxy-2β-triphenylmethoxymethyltetrahydropyran (5.80g), m.p. 79°–83° C. [NMR: s,1.58; s,2.76; s,2.80; s,3.36; m,3.37–3.50; s,3.46; m,7.20–7.35; m,7.45–7.50].

EXAMPLE 3

By proceeding in a manner similar to that hereinbefore described in Example 1, but replacing the ethanol by isopropanol (50 ml), there was prepared 3α,4β-dihydroxy-5β-iodo-6α-isopropoxy-2β-triphenylmethoxymethyltetrahydropyran (6.69 g), m.p. 125°–129° C. [NMR: d,1.13; d,1.18; s,1.57; d,2.36; d,2.47; s,2.76; m,3.37–3.50; s,5.30; m,7.20–7.35; m,7.45–7.50].

EXAMPLE 4

By proceeding in a manner similar to that hereinbefore described in Example 2, but replacing the methanol by isopropanol (2 g), there was prepared 3α,4β-dihydroxy-5β-iodo-6α-isopropoxy-2β-triphenylmethoxymethyltetrahydropyran (5.51 g), m.p. 123°–127° C. [NMR: d,1.18; d,1.21; s,1.58; s,2.76; s,2.80 m,3.37–3.50; s,3.41: q,4.31: m,7.20–7.35; m,7.45–7.50].

EXAMPLE 5

By again proceeding in a manner similar to that hereinbefore described in Example 2, but replacing the N-iodosuccinimide by N-bromosuccinimide (3.1 g), there was prepared 3α,4β-dihydroxy-5β-bromo-6α-methoxy-2β-triphenylmethoxymethyltetrahydropyran (5.23 g), m.p. 92°–96° C. [NMR: s,1.57; d,2.39; d,2.41; s,2.76; s,3.36; m,3.37–3.50; s,5.09; m,7.20–7.35; m,7.45–7.50].

EXAMPLE 6

By proceeding in a manner similar to that hereinbefore described in Example 4, but replacing the N-iodosuccinimide by N-bromosuccinimide (3.1 g), there was prepared 3α,4β-dihydroxy-5β-bromo-6α-isopropoxy-2β-triphenylmethoxymethyltetrahydropyran (5.72 g), m.p. 99°–103° C. [NMR: d,0.85; d,1.11; s,1.57; d,2.39; d,2.41; s,2.76; m,3.37–3.50; m,7.20–7.35; m,7.45–7.50].

EXAMPLE 7

A solution of 3α,4β-dihydroxy-5β-iodo-6α-methoxy-2β-triphenylmethoxymethyltetrahydropyran (5.4 g) in ethyl acetate (100 ml) was treated with triethylamine (2 ml) and damp Raney nickel paste (1 g). The mixture was shaken in a hydrogen atmosphere at 40 psig for 21.5 hours at the ambient temperature. The catalyst was then filtered off and washed with ethyl acetate (100 ml). The combined solutions were washed with water (50 ml) and evaporated to dryness, to give 3α,4β-dihydroxy-6α-methoxy-2β-triphenylmethoxymethyltetrahydropyran (3.83 g), m.p. 136°–140° C. [NMR: s,1.59; d,1.63; d,1.67; q,2.12; d,2.41; d,2.70; s,3.30; m,3.35–3.45; m,3.57–3.63; d,4.46; d,4.78; m,7.20–7.35; m,7.45–7.50].

EXAMPLE 8

A solution of 3α,4β-dihydroxy-5β-iodo-6α-methoxy-2β-triphenylmethoxymethyltetrahydropyran (5.4 g) in ethyl acetate (100 ml) was treated with triethylamine (2 ml) and damp palladium on charcoal paste catalyst (5% w/w; 1 g). The mixture was shaken in a hydrogen atmosphere at 40 psig for 24 hours at the ambient temperature. The catalyst was then filtered off and washed with ethyl acetate (100 ml). The combined solutions were washed with water (2×20 ml) and to dryness, to give 3α,4β-dihydroxy-6α-methoxy-2β-triphenylmethoxymethyltetrahydropyran (2.8 g), m.p. 134°–138° C. [NMR: s,1.59; d,1.63; d,1.66; q,2.10; d,2.41; d,2.71; s,3.30; m,3.37–3.45; m,3.57–3.63; d,4.46; d,4.78; m,7.20–7.35; m,7.45–7.50].

We claim:

1. A compound of the general formula:

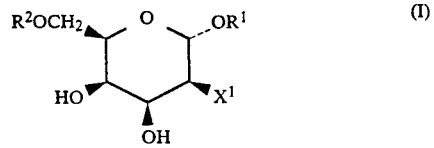

wherein $R^1$ represents a straight- or branched-chain alkyl group containing from 1 to 4 carbon atoms, $R^2$ represents an acid-labile protecting group and $X^1$ represents a halogen atom.

2. A compound according to claim 1 wherein $R^1$ represents a methyl or isopropyl group.

3. A compound according to claim 1 wherein $R^2$ represents a triphenylmethyl group.

4. A compound according to claim 1 wherein $X^1$ represents a bromine or iodine atom.

5. A compound according to claim 2 wherein $R^2$ represents a triphenylmethyl group.

6. A compound according to claim 2 wherein $X^1$ represents a bromine or iodine atom.

7. A compound according to claim 3 wherein $X^1$ represents a bromine or iodine atom.

8. A compound according to claim 5 wherein $X^1$ represents a bromine or iodine atom.

* * * * *